(12) United States Patent
Dubey et al.

(10) Patent No.: US 6,717,007 B1
(45) Date of Patent: Apr. 6, 2004

(54) REGIOSPECIFIC SYNTHESIS OF PHOSPHONOUS ACIDS

(75) Inventors: Sushil Kumar Dubey, Mandideep (IN); Venkat Rajgopal, Mandideep (IN); Anil Vir Singh, Mandideep (IN); Saswata Lahiri, Mandideep (IN); Mukesh Jagannath Wani, Mandideep (IN)

(73) Assignee: Lupin Limited (IN)

( * ) Notice: Subject to any disclaimer, the term of this patent is extended or adjusted under 35 U.S.C. 154(b) by 0 days.

(21) Appl. No.: 10/088,381

(22) PCT Filed: Sep. 16, 1999

(86) PCT No.: PCT/IN99/00049
§ 371 (c)(1),
(2), (4) Date: Aug. 5, 2002

(87) PCT Pub. No.: WO01/19837
PCT Pub. Date: Mar. 22, 2001

(51) Int. Cl.⁷ .................................................. C07F 9/28

(52) U.S. Cl. .......................................................... 562/8

(58) Field of Search ................................ 562/8, 11, 23, 562/24

(56) References Cited

U.S. PATENT DOCUMENTS

| | | | | |
|---|---|---|---|---|
| 4,485,052 A | * | 11/1984 | Kleiner et al. | 562/8 |
| 4,590,014 A | * | 5/1986 | Wolf et al. | 562/8 |
| 4,740,332 A | * | 4/1988 | Thottathil | 562/8 |
| 6,359,171 B1 | * | 3/2002 | Weferling et al. | 562/8 |
| 6,534,673 B1 | * | 3/2003 | Weferling et al. | 562/8 |

* cited by examiner

*Primary Examiner*—Jean F. Vollano
(74) *Attorney, Agent, or Firm*—Pendorf & Cutliff (57) ABSTRACT

An improved regiospecific synthesis of organic phosphonous acids, comprising of hydrophosphorylation of an olefin with hydrophosphorous acid in the presence of an inorganic persulfate, which acts as a source of free radicals at a pH ranging from 4.5 to 7.0, in which the orientation of addition is anti-Markonikoff. The process enables production of organic phosphonous acids at lower temperature and atmospheric pressure under milder pH conditions for better regioselectivity in hydrophosphorylation and obtain the phosphonous acid with good yield and purity following simple isolation procedure. Phosphonous acids obtained by the process are commercially valuable as effective detergents and wetting agents, lubricants and lubricant additives, plasticizers for plastics and resins, corrosion inhibitors, chemicals including insecticides and pesticides, cobalt extractants and as key intermediates for preparation of commercially important angiotensin converting enzyme (ACE) inhibitors.

9 Claims, 3 Drawing Sheets

REGIOSPECIFIC SYNTHESIS OF PHOSPHONOUS ACIDS

CROSS REFERENCE TO RELATED APPLICATION

This application is a national stage of PCT/IN99/00049 filed Sep. 16, 1999, published as WO 01/19837 A1 on Mar. 22, 2201.

FIELD OF THE INVENTION

This invention relates to an improved process for preparing organic phosphonous acids. More specifically the invention relates to regiospecific synthesis of organic phosphonous acids of formula (I), conforming to anti-Markonikoff addition, (I)

where $R^1$ is straight or branched alkyl of 1 to 10 carbon atoms; alkyl substituted with halogen, trifluoromethyl, hydroxy, alkoxy, carboxy and amino groups; cycloalkyl of 3 to 7 carbon atoms; phenyl substituted with halogen, trifluoromethyl, hydroxy, amino, alkyl and alkyl substituted by halogen, trifluoromethyl, hydroxy, alkoxy, carboxy and amino groups; carboxylic acid or carboxylic acid ester; cyano; aldehyde; and a substituted five or six membered heterocyclic ring system, wherein the heteroatom is nitrogen, oxygen or sulfur and the substituent is an alkyl or carboxylic acid group; all of which may additionally contain functional groups sensitive to acidic conditions.

BACKGROUND ART

Phosphonous acids are commercially valuable as effective detergents and wetting agents, lubricants and lubricant additives, plasticizers for plastics and resins, corrosion inhibitors, chemicals including insecticides and pesticides, cobalt extractants and as key intermediates for preparation of commercially important angiotensin converting enzyme (ACE) inhibitors such as Ceranopril as disclosed in U.S. Pat. No. 4,452,790 and Fosinopril as disclosed in U.S. Pat. No. 4,337,201.

THE KNOWN ART OF SYNTHESIS OF PHOSPHONOUS ACIDS

A. Synthesis of organic phosphonous acids involve formation of a carbon-phosphorous linkage and in most of the early methods this was obtained by reactions of phosphorous-halogen compounds, such as:
  a. reaction of alkyl halides with phosphine or by use of Grignard reagents.
  b. reaction of phosphorous trichloride with an alcohol, followed by necessary isomerisation as described in J. Gen. Chem., (USSR), 4, 898–900 (1934).
  c. reaction of phosphorous trichloride or phosphorous pentachloride with an olefin to form a phosphorous containing alkyl halide which on reaction with phosphorous pentoxide affords unsaturated phosphonates as disclosed in U.S. Pat. No. 2,425,766 and in J. Am. Chem. Soc., 67, 1864 (1945).

However, these methods have not found any commercial application due to use of hazardous chemicals, use of Grignard reagents, complex reactions involved, and poor yields.

B. Later preparative methods utilised the hydrophosphorylation of olefins for forming the carbon-phosphorous bond. This involved reaction of olefins with hypophosphorous acid or its salts or esters thereof in the presence of free radical initiators (usually organic peroxides) to give the corresponding phosphonous acid, its salts or dialkyl phosphonates. The reaction may be summarised as follows:

R may be alkyl, substituted alkyl, aryl, substituted aryl, arylalkyl, carboxylic acid or carboxylic acid ester, cyano, aldehyde etc.; A may be hydrogen, hydroxy or alkoxy, and B may be hydroxy, alkoxy or $OM^+$, wherein M is sodium, potassium or calcium.

Such methods have been described in J. Am. Chem. Soc., 77, 3411 (1955); Org. Reactions, 13, 150 (1963); J. Chem. Soc. Jpn., Ind. Chem. Sect., 68, 2080, A 112–113 (1965); J. Gen. Chem. (USSR), 37, 1293 (1967); Metody Issled. Org. Soedin., 19, 42, (1968); Usp. Khim., 47, 1565 (1978); U.S. Pat. No. 2,724,718; British Patent No. 660,918; U.S. Pat. No. 2,726,256; and U.S. Pat. No. 2,957,931.

In the methods described above the phosphonous acids were generally prepared employing high pressure reaction conditions (using autoclaves) and higher temperatures (120° C.–300° C.), which entails severe limitations on the operability of a commercial process. Moreover, longer duration of reaction (2–50 hours), moderate yields (15–70%), formation of polymeric materials, especially the dimeric compound (20–50%), as major by-products are further limitations imposed upon commercial applicability. In addition, isolation of the pure product is usually tedious. In most of the methods high vacuum distillation is employed, which further render the processes hardly practical.

The general reaction conditions described above were utilised for preparation of various phosphonous acids, which find other applications as well. Thus, U.S. Pat. No. 2,648,695, describes preparation of a phostone, obtained by heating a phosphonous acid. The phosphonous acids were in turn prepared by hydrophosphorylation of a hydroxy substituted olefin in the presence of an organic peroxide at 130° C.

Phostones are valuable intermediates for synthesis of polyfunctional phosphinic acids.

100–150° C.

(Phostone)

Yields are not reported in the patent and the hydrophosphorylation is carried out at higher temperature.

U.S. Pat. No. 4,108,889 discloses preparation of long-chain non-terminally substituted alkane phosphonic acids, useful as detergents which involves isomerisation of an α-olefin to an internally unsaturated olefin using a macroreticular strong acid cation exchange resin, followed by reaction of the non-terminal alkene thus produced with a dialkyl phosphite in the presence of a free radical intiator at 135°–140° for 5–6 hours to form the diester, which is hydrolysed to the phosphinic acid. i-$C_nH_{2n}$ and i-$C_nH_{2n+1}$ stand for internally unsaturated olefin and non-terminally substituted alkane respectively and n ranges from 12 to 22 and X is Cl or Br.

Moisture of the resin used, temperature of isomerisation are critical parameters which determine the yield and amounts of dimeric compounds limiting the general applicability of the method. In addition, the hydrophosphorylation is carried out at higher temperature.

U.S. Pat. No. 4,185,031 describes preparation of numerous fluorinated phosphinic acids, useful as grease thickeners for liquid lubricants by reaction of fluorinated olefins and an acid containing one or more phosphorous hydrogen bonds in the presence of organic peroxides at 70° C. to 80° C. for 8 hours to 4 days. No yields are reported.

(1)

(2)

U.S. Pat. No. 4,321,213 and U.S. Pat. No. 4,374,780 disclose preparation of certain 2,4,4, trimethyl pentyl phosphinic acids, useful as cobalt extractants obtained by free radical reaction of mono-2,4,4'-trimethyl pentyl phosphine to an olefin in an autoclave, to form the carbon-phosphorous linkage, followed by oxidation with hydrogen peroxide to the phosphinic acids.

The reaction conducted at high pressure (550 psig) generally gives a complex mixture of products, from which the desired phosphinic acid is separated by distillation techniques.

These methods also suffer from similar limitations mentioned earlier.

C. Simplification of or improvements in the process were reported, which are as follows:

Nifantev et al. [Zhu. Obs. Khim., 50 (8), 1744–1752 (1980)] demonstrated that hydrophosphorylation of olefins could be carried out at atmospheric pressure and at lower temperatures (75–85° C.) using sodium or potassium hypophosphite in the presence of an organic peroxide in aqueous dioxane. They used small excess of a mineral or organic acid and claimed faster reaction rates.

The reactions took 4–7 hours for completion. Moreover, the method would not be suitable for preparing phosphonous acids containing acid-sensitive groups.

Kleinar et al (U.S. Pat. No. 3,812,222) reported that alkane phosphonic acid diesters could be obtained in high yield (90–95%) if the reaction is conducted using α-olefins which are sulfur free or nearly sulfur free.

However, higher temperatures (130° C.–250° C.) required for the reaction is a major limitation.

Wolf et al (U.S. Pat. No. 4,90,014) prepared mono- and bis-alkyl phosphinates by simultaneous addition of alcoholic solution of an olefinic compound and all of the radical source (organic peroxide) to a hot alcoholic solution (78–80° C.) of hyphophosphite at atmospheric pressure.

However, duration of the reaction is longer (5–55 hrs.) eventhough moderate to high yields (56–92%) were obtained.

The same inventors (Wolf et al, U.S. Pat. No. 4,632,741) carried out the reaction under ultraviolet irradiation in the presence of a photoinitiator (aldehydes or ketones). Phosphinate salts or bis(alkyl) phosphinate salts were obtained in a yield of 89–99%.

However, use of ultraviolet irradiation would require sophisticated instrumentation adding to the cost of the process.

Thottathil (U.S. Pat. No. 4,740,332) claims a mild process which besides avoiding high pressure could be conducted at lower temperatures (40–120° C.). The hydrophosphorylation was carried out using hypophosphorous acid or sodium hypophosphite in the presence of azobisisobutyronitrile in an alcoholic solvent at a pH ranging from below 1.0 to 4.0. A strong acid was added to attain the acidic pH when sodium hypophosphite was employed.

Apart from longer duration of reaction (18–20 hrs.), this method would not be suitable when phosphonous acids containing acid-sensitive groups have to be prepared.

To summarise, the prior art methods disscussed hereinbefore are associated with various shortcomings, which limit their application as a suitable method for preparing various phosphonous acids. The basic shortcomings are:

a. employment of high pressure (as high as 550 psig) and high temperatures (100° C.–300° C.).
b. longer duration of reactions (2–50 hrs).
c. formation of polymeric materials in varying amounts, which affect the yield and purity.
d. lower regioselectivity obtained.
e. tedious isolation and purification procedure, usually involving high vacuum distillation techniques.
f. acidic conditions of the reaction, not suitable when olefins containing acid-labile groups are employed.

Thus, a need exists for an improved method for preparing organic phosphonous acids, which would reduce or eliminate the limitations associated with prior art methods and which is mild, convenient, regiospecific, cheap and safe.

SUMMARY OF INVENTION

Thus the present invention relates to an improved regiospecific process for preparing phosphonous acids of formula (I), conforming to anti-Markonikoff addition, (I)

where $R^1$ is straight or branched alkyl of 1 to 10 carbon atoms; alkyl substituted with halogen, trifluoromethyl, hydroxy, alkoxy, carboxy and amino groups; cycloalkyl of 3 to 7 carbon atoms; phenyl substituted with halogen, trifluoromethyl, hydroxy, amino, alkyl and alkyl substituted by halogen, trifluoromethyl, hydroxy, alkoxy, carboxy and amino groups; carboxylic acid or carboxylic acid ester; cyano; aldehyde; and a substituted five or six membered heterocyclic ring system, wherein the heteroatom is nitrogen, oxygen or sulfur and the substituent is an alkyl or carboxylic acid group; all of which may additionally contain functional groups sensitive to acidic conditions, comprising reacting an olefin of formula (II),

$R^1$—CH=CH$_2$ (II)

wherein $R^1$ is as defined above, with hypophosphorous acid in presence of a water-miscible organic solvent and an inorganic persulfate of formula (III), (III)

wherein M is ammonium, sodium or potassium, at a temperature in the range of 60° C. to 80° C. for 15–60 minutes at atmospheric pressure at a pH within the range of from below 1.0 to 7.0, and recovering the said phosphonous acid formed from the reaction mixture.

The reaction may be summarised as follows.

where R1 and M are as defined hereinbefore.

After completion of the reaction, the product is isolated via a simple work up method.

The process of this invention may also be applied for preparing phosphonous acids by hydrophosphorylation of non-terminal olefins of structure, wherein $R^1$ is as defined hereinbefore and $R^2$ is selected from alkyl, substituted alkyl, substituted aryl, arylalkyl, and a carboxylic acid or carboxylic acid ester group in a water-miscible organic solvent as mentioned above at 60–80° C. at a pH ranging from below 1.0 to 7.0. However, the reaction exhibits increased regiospecificity in providing the desired isomer when a pH within the range from 4.5 to 7.0, preferbaly within the range from 6.0 to 7.0 is employed.

The term 'alkyl' in the context of the present invention refers to straight chain or branched chain groups having 1 to 10 carbon atoms, or a cycloalkyl group.

The term 'substituted alkyl' refers to alkyl group substituted with halogen, another alkyl group, hydroxy, alkoxy, amino, carboxy or trifluoromethyl groups.

The term 'substituted aryl' refers to phenyl substituted with halogen, trifluoromethyl hydroxy and amino group.

The term 'cycloalkyl' refers to groups having 3 to 7 carbon atoms such as cyclopropyl, cyclobutyl, cyclopentyl, cyclohexyl or cycloheptyl.

The term 'arylalkyl' refers to phenyl substituted with 'alkyl' or 'substituted alkyl'. The terms 'alkyl' and 'substituted alkyl' are as defined hereinbefore.

The term 'subsitituted heterocyclic ring system' refers to five or six membered heterocyclic ring substituted by an alkyl or carboxyl group, wherein the heteroatom could be nitrogen, oxygen or sulfur.

The olefins employed as substrates in the present invention are compounds of formula (II), wherein $R^1$—CH=CH$_2$ (II)

$R^1$ is alkyl, substituted alkyl, substituted aryl, arylalkyl, carboxylic acid or caboxylic acid ester, cyano, aldehyde and a substituted five or six membered heterocyclic ring system, all of which may additionally contain acid sensitive functional groups.

Olefins of structure, wherein $R^1$ is as defined above and $R^2$ may be alkyl, substituted alkyl, substituted aryl, carboxylic acid or carboxylic acid ester group, may also be employed as substrates for the process of this invention.

Example of olefins preferred as starting materials in carrying out the present invention include, but are not limited to.

4-phenyl-1-butene, cyclohexene, methylene cyclohexane, ehtyl 2,4-dimethyl-2-pentenoate and N-tert butyl-(2S)-2-(prop-2-enyloxy carbonyl)-pyrrolidine carboxylate.

Hypophosphorous acid, employed in the present invention is usually used as a 30–50 wt % solution in water.

The molar ratio of hypophosphorous acid to the olefin employed is within the range of 1:1 to 10:1, preferably in a molar ratio greater than 3:1 and most preferably within the range of 3:1 to 5:1. Employment of hypophosphorous acid in excess of 3 molar equivalent is beneficial in that the formation of dimeric material is reduced, thereby affording the organic phosphonous acid in better yields, possessing higher purity.

Organic bases selected from triethylamine, tri-n-butylamine and N-methyl morpholine are usually employed for adjustment and maintenance of pH during the reaction. Triethylamine is the preferred base.

The process uses inorganic persulfates as free radical initiators, which is novel. The use of inorganic persulfates of formula (III), namely ammonium, sodium and potassium persulfate as free radical initiators in the process is novel, which forms an embodiment of the present invention.

The inorganic persulfates are usually employed in catalytic amounts or in a molar proportion to the olefin within the molar ratio from 0.2:1 to 1:1, the preferred range being from 0.2:1 to 0.5:1.

The reaction could also be carried out in presence of water-miscible organic solvents both protic and aprotic.

The reaction is fast and is usually complete in about 15–60 minutes time.

Moreover, the product is isolated by a simple work up procedure.

The process is best carried out in a homogeneous medium and sufficient quantity of the solvent is used to keep all the reactants in homogeneous phase. Usually about 2 to 20 times by volume of the solvent relative to the quantity of olefin is employed in the process.

The advantage of the present process over that described in the prior art is that depending on the nature of the olefin used, several water-miscible organic solvents, both protic and aprotic could be employed, examples of which include but are not limited to acetone, acetonitrile, ethanol, methanol, and N,N-dimethyl formamide.

The reaction could be conducted at atmospheric pressure and at a lower temperature within the range from 60° C. to 80° C., optimally at the reflux temperature of the solvent employed.

In the process of the invention one may thus avoid the use of higher pressures and higher temperatures. The process of the present invention can be carried out in a wide pH range from acidic (1.0 or below) to neutral (i.e. pH 7.0). However, milder the pH the better is the efficacy of the reaction. A pH within the range from 4.5 to 7.0 is preferred. Even though the process of this invention can be carried out at a wide range of pH, ranging from below 1.0 to pH 7.0, better results are obtained at a pH within the range from 4.5 to 7.0 and most preferably within the range from 6.0 to 7.0.

The milder pH conditions have the following advantages in that a. formation of by-products, especially the dimer is reduced.

b. olefins containing functional groups sensitive to acidic conditions could be employed.

c. better regioselectivity in hydrophosphorylation is achieved.

The other advantages are that since the decomposition products of inorganic persulfates being water soluble, these can be easily removed from the reaction mixture enabling easier work-up and isolation of phosphonous acids in higher purity. Secondly, inorganic persulfates are cheaper compared to organic peroxides and offer cost advantages.

The present invention thus enables one to carry out hydrophosphorylation of an olefin, both terminal and non-terminal, which may additionally contain acid-sensitive functional groups.

a. in the presence of inorganic persulfates, which enhance the rate of reaction.

b. under milder pH conditions which leads to formation of minimum amount of dimer, which does not affect acid-sensitive functional groups contained in the olefin, and which produces better regioselectivity, conforming to anti-Markonikoff addition.

c. at lower temperatures and at atmospheric pressure and d. isolating the product in a simple manner.

The following non-limiting examples are illustrative of the invention and are especially preferred embodiments. Chemical shifts in the $^{31}P$ NMR spectra are calibrated with respect to that of triphenyl phosphine as standard ($\delta$-5.3 in $CDCl_3$).

EXAMPLE 1

4-Phenylbutyl Phosphonous Acid (Using Acetonitrile as Solvent, and pH of 6.5±0.5)

To a 30 wt % aqueous solution of hypophosphorous acid (41.8 ml, 0.19 moles) in acetonitrile (100 ml) was added 4-phenyl-1-butene (5 gm, 0.038 moles) and sodium persulfate (1.8 gm, 0.00756 moles). To the stirred mixture triethylamine was added and the pH of the reaction mixture was adjusted to 6.5±0.5. The reaction mixture was heated at 77° C. for 15 minutes for the reaction to be complete. Acetonitrile was distilled off at 40° C. under vacuum and the reaction mixture was diluted with water (20 ml). The pH of the mixture was adjusted to 8.5 with 50% aqueous sodium hydroxide followed by acidification to a pH of 5.0±0.2. The aqueous medium was extracted with dichloromethane (20 ml) and kept aside. The pH of the aqueous layer was adjusted to 1–1.5 using conc. $H_2SO_4$ and reextracted with dichloromethane (2×20 ml). The total organic layers were combined, dried over anhydrous sodium sulfate and the solvent distilled off to yield 6.6 gm (88.0%) of the title compound as an oil, having a purity 97.6%.

IR (Neat): 2933.1, 1495.9, 1453.7, 1173.7, 973.6 $Cm^{-1}$; $^1H$ NMR($CDCl_3$): $\delta$ 10.68 (S, 1H, —OH); 8.34–5.64 (d, 1H, J=542 Hz, P—H); 7.25–7.06 (m, 5H, aromatic protons); 2.56 (t, 2H, Ph—CH2—); 1.77–1.47 (m, 6H, C-1, C-2 and C-3 protons); $^{13}C$ NMR($CDCl_3$) $\delta$ 141.7, 128.3, 125.8 (aromatic ring carbons); 35.4 (Ph—$\underline{C}H_2$—); 32.10 (d, Jcp=16 Hz, C-2); 29.0 (d, Jcp=94 Hz, C-1), 20.3 (C-3); $^{31}P$ NMR($CDCl_3$): $\delta$ 37.60.

EXAMPLE 2

4-Phenylbutyl Phosphonous Acid (Using Acetone as Solvent, and pH of 6.5±0.5)

To 30 wt % aqueous solution of hypophosphorous acid (41.8 ml, 0.19 moles) in acetone (100 ml) was added 4-phenyl-1-butene (5 gm, 0.038 moles) and sodium persulfate (1.8 gm, 0.00756 moles). The pH of the mixture was adjusted to 6.5±0.5 with triethylamine and then heated at 77° C. for 15 minutes.

The reaction mixture was worked up exactly the same way as described in Example 1 to give 6.25 gm (86.6%) of the title compound as an oil, having a purity of 97.5%.

EXAMPLE 3

4-Phenylbutyl Phosphonous Acid (Using Ethanol as Solvent, and pH of 6.5±0.5)

To a 30 wt % aqueous solution of hypophosphorous acid (41.8 ml, 0.19 moles) in ethanol (100 ml) was added 4-phenyl-1-butene (5 gm, 0.038 moles) and sodium persulfate (1.8 g, 0.00756 moles). The pH of the mixture was adjusted to 6.5±0.5 with triethylamine and then heated at 77° C. for 15 minutes.

The reaction mixture was worked up exactly the same way as described in Example 1 to give 6.50 gm (86.6%) of the title compound as an oil, having a purity of 97.5%.

EXAMPLE 4

4-Phenylphosphonous Acid (Using Acetonitrile as Solvent, and pH of 4.5–5.0)

To a 30 wt % aqueous solution of hypophosphorous acid (41.8 ml, 0.19 moles) in acetonitrile (100 ml) was added 4-phenyl-1-butene (5 gm, 0.038 moles) and sodium persulfate (1.8 gm, 0.00756 moles). The pH of the mixture was adjusted to 6.5±0.5 with triethylamine and then heated at 77° C. for 15 minutes.

The reaction mixture was worked up exactly the same way as described in example 1 to give 6.0 gm (80%) of the title compound as an oil, having a purity of 96.5%.

EXAMPLE 5

Cyclohexyl Phosphonous Acid

To a 30 wt % aqueous solution of hypophosphorous acid (67.10 ml, 0.305 moles) in acetonitrile (100 ml) was added cyclohexene (5 gm, 0.061 moles) and sodium persulfate (1.0 gm, 0.0122 moles). The pH of the mixture was adjusted to 6.5±0.5 with triethylamine and then heated at 77° C. for 15 minutes.

The reaction was worked up exactly the same way as described in Example 1 to give 2.7 gm (30%) of the title compound as an oil.

IR (Neat): 2928.8, 2350.4, 1449.7, 1214.0, 970.5 cm$^{-1}$; $^1$HNMR (CDCl$_3$): δ 11.0 (bs, 1H, —OH); 8.15–5.45 (d, 1H, J=540 HZ, P—H); 2.0–1.5 (m, 6H); 1.45–1.1 (m, 5H); $^{FPAA/55(PCT)}$ Cl$_3$): δ 36.9(d, Jcp=96 Hz, C-1); 25.5 (d, J=12 Hz, C-2 and C-6), 23.7 (C-3, C-4 and C-5); $^{31}$PNMR (CDCl3): δ 40.28.

EXAMPLE 6

[3'-(Hydrohydroxyphosphoryl)propyl]-1-(tert-butyloxycarbonyl)pyrrolidine-2(S)-carboxylate To a 30 wt % aqueous solution of hypophosphorous acid (4.62 ml, 0.021 moles) in acetonitrle (20 ml) was added N-tert-butyl-(2S)-2-(prop-2-enyloxycarbonyl)-pyrrolidine-carboxylate (1 gm, 0.00418 moles) and sodium persulfate (0.20 g, 0.000836 moles).The pH of the mixture was adjusted to 6.5±0.5 with triethylamine and then heated at 77° C. for 15 minutes.

The reaction mixture was worked up exactly the same way as described in Example 1 to give 0.7 gm (52%) of the title compound as an oil.

IR (Neat): 2976.8, 2362.9, 1754.4, 1696.2, 1399.6, 1161.2, 974.0 cm$^{-1}$; $^1$HNMR (CDCl$_3$) at 25° C.: δ 8.4–5.7 (d, 1H, J=542 Hz, P—H); 4.3–4.05 (m, 3H, H-1'$_{a,b}$, H-2); 3.55–3.20(m, 2H, H-5$_{a,b}$); 2.25–1.60 (m, 8H, H-3$_{a,b}$, H-4$_{a,b}$, H-2'$_{a,b}$, H-3'$_{a,b}$); 1.35 (d, 9H). $^{13}$CNMR (CDCl$_3$) at 25° C.: (δ) 173.0, 172.8 (Ester carbonyl); 154.4, 153.7 (Amide carbonyl); 79.9(C—(CH$_3$)$_3$); 64.5, 64.2 (C-1'); 59.0, 58.8 (C-2) 46.5, 46.3 (C-5); 30.8, 29.9 & 24.3, 23.6(C-3 & C-4); 28.3 (C—(CH$_3$)$_3$); 27.0, 25.2 (C-3'); 20.4 (C-2'); $^{31}$PNMR (CDCl3) at 25° C.: δ 36.68, 36.1.

EXAMPLE 7

2,3-Dimethyl-but-2yl-phosphinic Acid

To a 30 wt % aqueous solution of hyphophosphorous acid (13.2 ml, 0.06 moles) in acetonitrile (20 ml) was added 2,3-dimethyl-2-butene(1 gm, 0.012 moles) and sodium persulfate (0.57 gm, 0.0024 moles). The pH of the mixture was adjusted to 6.5±0.5 with triethylamine and then heated at 77° C. for 15 minutes.

The reaction mixture was worked up exactly the same way as described in Example 1 to give 0.55 gm (31%) of the title compound as an oil.

IR (Neat): 2351, 1383, 1204, 996 cm$^{-1}$; $^1$HNMR (CDCl$_3$): δ 11.3 (bs, 1H, —OH); 8.15–5.48(d, 1H, J=530 Hz, P—H), 2.0–1.8 (m, 1H, —CH(CH$_3$)$_2$); 1.02 (s, 3H), 0.93 (d, 6H), 0.89 (s, 3H). $^{13}$CNMR (CDCl$_3$): δ 36.6 (d, Jcp=94 Hz, P—C(CH$_3$)$_2$, 31.7(CH(CH$_3$)$_2$), 17.57, 17.25. $^{31}$PNMR(CDCl3): δ 48.16.

EXAMPLE 8

Cyclohexylmethyl Phosphinic Acid

To a 30 wt % aqueous solution of hypophosphorous acid (11.50 ml, 0.052 moles) in acetonitrile (20 ml) was added methylene cyclohexane (1 gm, 0.014 moles) and sodium persulfate (0.495 g, 0.0021 moles) The pH of the reaction mixture was adjusted to 6.5±0.5 and heated at 77° C. for 15 minutes.

The reaction mixture was worked up exactly the same way as in Example 1 to give 1.2 gm (71%) of the title compound as an oil.

IR (Neat): 2380, 1283, 1204, 953 Cm$^{-1}$ $^{FPAA/55\ (PCT)}$; $^1$HNMR (CDCl$_3$): δ 11.25 (bs, 1H, —OH); 8.4–5.7(d, 1H, J=540 Hz, P—H); 1.8–1.4 (m, 8H); 1.3–0.8 (m, 5H). $^{13}$CNMR (CDCl$_3$): δ 36.9 (d, Jcp=96 Hz, P—CH$_2$—), 34.4, 31.7, 25.9; $^{31}$PNMR(CDCl3): δ 36.37.

EXAMPLE 9

Cyclohexylmethyl Phosphinic Acid

Methylene cyclohexane (1 g, 0.0104 moles) was reacted exactly as in Example 8 but pH was maintained at 0–0.4 instead of 6.5±0.5 to give 1 gm (59.2%) of title compound as an oil.

EXAMPLE 10

Ethyl 3-(Hydrohydroxy Phosphoryl)-2-,4-dimethyl Pentanaoate

To a 30 wt % aqueous solution of hypophophorous acid (7.05 ml, 0.032 moles) in acetinitrile (20 ml) was added ethyl 2,4-dimethyl-2-pentenoate (1 gm, 0.00641 moles) and sodium persulfate (0.00128 moles, 0.305 g). The reaction mixture was heated 77° C. for 15 minutes after adjustment pH to 6.5±0.5 with triethylamine.

Work up of the reaction mixture in the same way as described in example 1 gave 0.80 gm (56.2%) of the title compound as an oil.

IR (Neat): 2966.1, 2369.9, 1731.2, 1466.7, 1186.4, 1059.0, 985.0 cm$^{-1}$; $^1$HNMR (CDCl$_3$): δ 8.62–5.85 and 8.52–5.8 (2d, 1H); 7.55 (bs, 1H); 4.1 (q, 2H); 3.0–2.7 (m, 1H); 2.2–1.85 (m, 2H); 1.35–1.15 (m, 6H); 1.15–0.9 (m, 6H). $^{31}$PNMR(CDCl3) δ 40.9, 39.88.

EXAMPLE 11

Ethyl 3-Hydroxyphosphoryl)-4-methylpentanoate (A) and Ethyl 2-(Hydrohydroxy Phosphoryl)-4-methylpentanoate (B)

To a 30 wt % aqueous solution of hypophophorous acid (7.8 ml, 0.0352 moles) in acetonitrile (20 ml) was added ethyl 4-methyl-2-pentenoate (1 g, 0.00704 moles) and sodium persulfate (0.335 9, 0.00141 moles). After adjusting the pH of the reaction mixture to 6.5±0.5 with triethylamine, it was heated at 77° C. for 15 minutes.

Work up in the same way as described in Example-1 afforded a mixture of title compounds(A) and (B) (0.9 gm, 61.4%) in a ratio of 88:12. The ratio of the individual isomers was determined by $^1$HNMR as well as by $^{13}$PNMR.

IR (Neat): 2963.9, 2365.4, 1734.2, 1466.2, 1372.9, 1162.5, 972.8cm$^{-1}$;

$^1$HNMR (CDCl$_3$): δ 9.1 (bs, 1H); 8.4–5.7 (d, 1H); 4.1 (m, 2H); 3.0–1.5(m, 4H); 1.3–1.5(m, 3H); 1.05–0.82 (m, 6H); $^{31}$PNMR(CDCl3) δ 40.9, 35.04.

EXAMPLE 12

Ethyl 3(Hydrohydroxy Phosphoryl)-4-methylpentanoate (A) and Ethyl 2-(Hydrohydroxy Phosphoryl)-4-methylpentanoate (B)

Ethyl 4-methyl-2-pentenoate (1 gm, 0.00704 moles) was reacted exactly as in example 11, but pH was maintained at 0–0.4 instead of 6.5±0.5 to give mixture of the title compounds A and B (0.6 gm, 41%) as an oil in a ratio of 76:24.

EXAMPLE 13

This example illustrates the advantage of employing an inorganic persulfate in the process. The rate of reaction is greatly enhanced when inorganic persulfates rather than organic peroxides are employed as free radical initiators.

In two separate experiments, an olefin of formula (II), wherein R$^1$ is C$_6$H$_5$—(CH$_2$)$_2$—, namely 4-phenyl-1-butene was subjected to hydrophosphorylation under identical conditions using hypophosphorous acid (5 eq. of olefin) in acetonitrile as solvent (20 ml /gm of olefin) at 77° C. at a pH of 6.5±0.5, employing (a) sodium persulfate (0.2 eq. of olefin) as free radical initiator in one case, and (b) azobisi-isobutryonitrile (AIBN, 0.2 eq. of olefin)) in the other.

In the case (a), a conversion greater than 80% to 4-phenylbutylphosphonous acid was achieved in 15 minutes time, whereas in the case (b), the reaction was found to be drastically slow. A conversion of about 80% was achieved only in about 5 hours time.

Moreover, even under acidic conditions, ie at a pH ranging from below 1.0 to a pH of 5.0, the persulfate mediated reaction was fast and took only 20 minutes to achieve a conversion greater than 80%, while under similar conditions the AIBN mediated one still took about 5 hours, the rate of which did not improve even after addition of extra amounts of AIBN.

Figure 1:
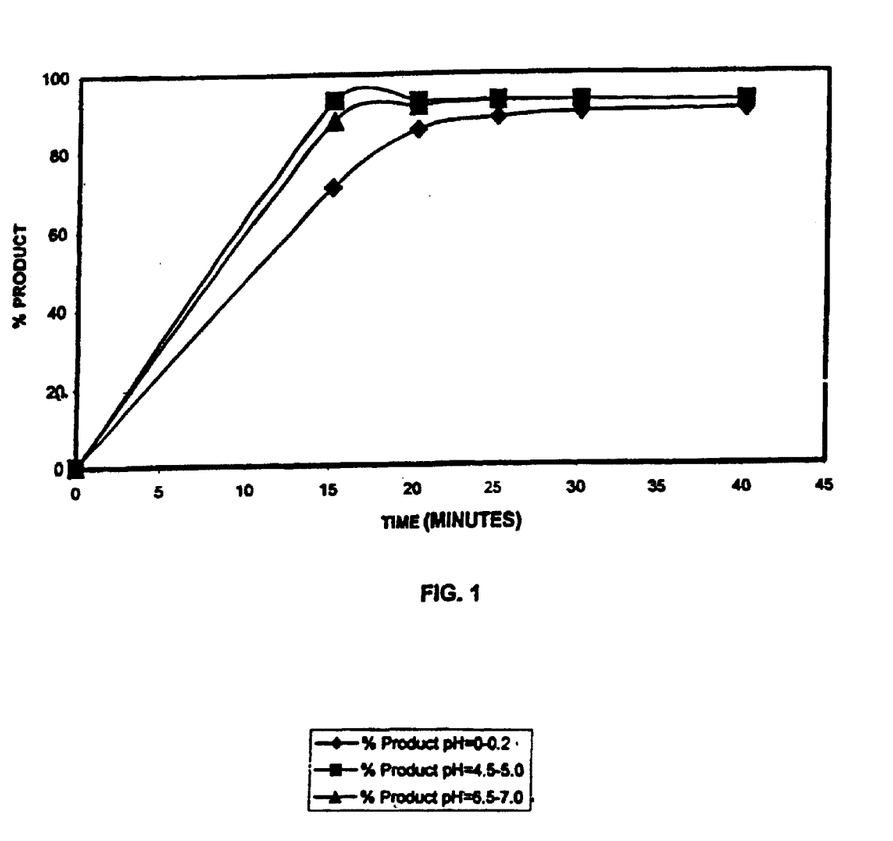
Figure 2:
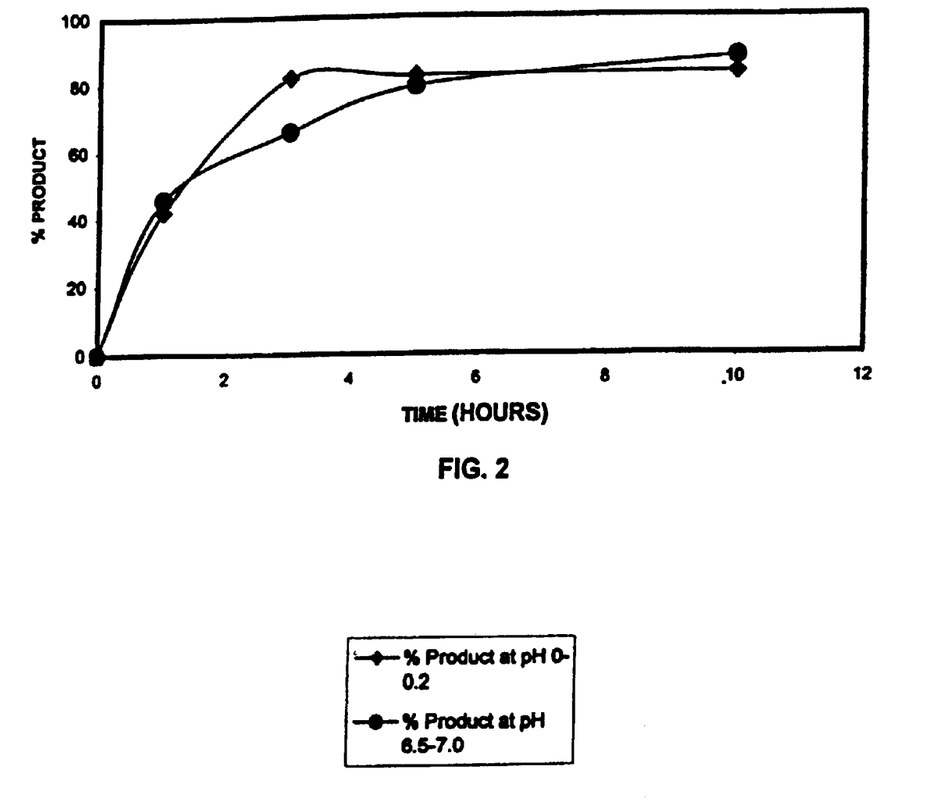

A comparative plot of the reaction rates versus time observed in hydrophosphorylation of 4-phenyl-1-butene using sodium persulfate and AIBN is depicted in FIG. 1 and FIG. 2 $_{FPAA/55(PCT)\ ly}$.

EXAMPLE 14

This example illustrates the advantage of using milder pH conditions in the process of the invention.

In the reaction of 4-phenyl-1-butene with hypophosphorous acid in the presence of acetonitrile and sodium persulfate carried out over a wide range of pH starting below 1.0 and upto 7.0, the amount of dimer formed is found to be maximum at a pH below 1.0 (Ca.5.3%) and minimum at a pH of 6.5 to 7.0(Ca.2.5%). Milder pH condition therefore is best suited to prepare phosphonous acids in better yield and higher purity.

Figure 3:
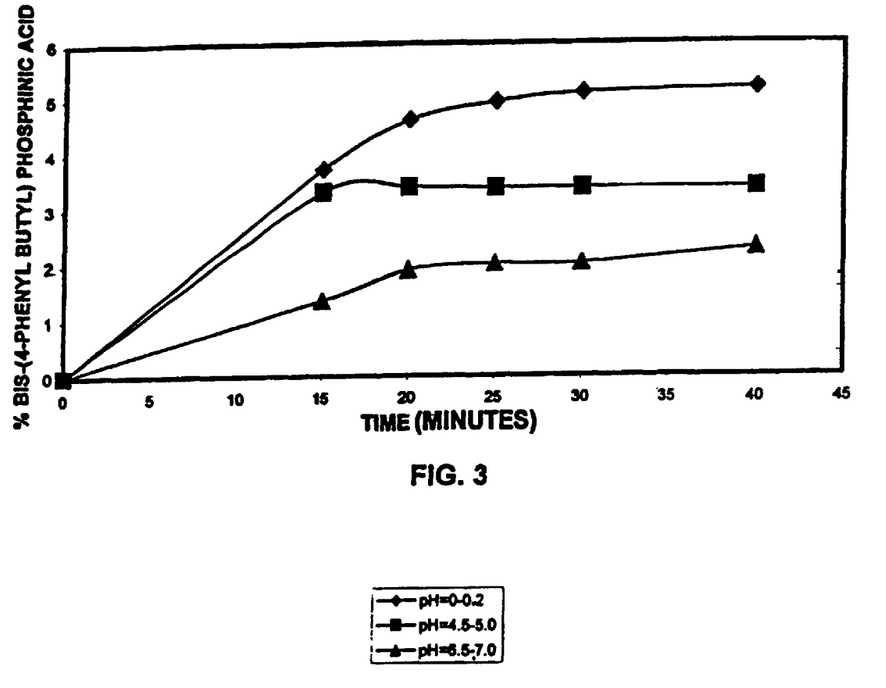

A plot depicting the percentage of formation of dimer vs time at different pH ranges in the hydrophosphorylation of 4-phenyl-1-butene is represented in FIG. 3.

Hydrophosphorylation of an olefin containing acid sensitive functional groups, like for example, N-tert-butyl(2S)-2-(prop-2-enyloxycarbonyl)-pyrrolidine carboxylate (IV) at a pH ranging from 6.5 to 7.0 gave the desired phosphonous acid (V), in which the acid-labile tert-butoxy carbonyl group is intact, as the major product. In carrying out the reaction at pH below 1.0 no hydrophosphorylation of the double bond was observed and the only reaction that took place was cleavage of the allyl group and hydrolysis of tert-butoxy carbonyl group, to give L-proline (VI) as the sole product

Improved regioselectivity to give one phosphonous acid isomer over the other on hydrophosphorylation of a non-terminal olefin at the preferred pH range of this invention is illustrated by the following example.

Ethyl 4-methyl-2-pentenoate gives a mixture of the 3-substituted phosphonous acid and the 2-substituted phosphonous acid in a ratio of 74:26, on hydrophosphorylation at a pH below 1.0. The regioselectivity of the reaction towards the 3-substituted isomer is increased by about 14% when a pH in the range of 6.5 to 7.0 is employed to give the 3- and 2-substituted isomers in a ratio of 88:12

We claim:

1. An improved regiospecific process for preparing phosphonous acids of formula (I), conforming to anti-Markonikoff addition, (I)

where $R^1$ is straight or branched alkyl of 1 to 10 carbon atoms; alkyl substituted with halogen, trifluoromethyl, hydroxy, alkoxy, carboxy and amino groups; cycloalkyl of 3 to 7 carbon atoms; phenyl substituted with halogen, trifluoromethyl, hydroxy, amino, alkyl and alkyl substituted by halogen, trifluoromethyl, hydroxy, alkoxy, carboxy and amino groups; carboxylic acid or carboxylic acid ester; cyano; aldehyde; and a substituted five or six membered heterocyclic ring system, wherein the heteroatom is nitrogen, oxygen or sulfur and the substituent is an alkyl or carboxylic acid group; wherein the process comprises reacting an olefin of formula (II), (II)

wherein $R^1$ is as defined above, with hypophosphorous acid in presence of a water-miscible organic solvent and an inorganic persulfate of formula (III), (III)

wherein M is ammonium, sodium or potassium, at a temperature in the range of 60° C. to 80° C. for 15–60 minutes at atmospheric pressure at a pH within the range of from 4.5 to 7.0, and recovering the said phosphonous acid formed from the reaction mixture.

2. A process according to claim 1, wherein the water-miscible organic solvent is selected from acetonitrile, acetone, ethanol, methanol and N,N-dimethyl formamide.

3. A process according to claim 1, wherein the reaction is carried out at a pH within the range from 6.0 to 7.0, the pH maintained by the addition of an organic base.

4. A process according to claim 1, wherein the reaction is carried out optimally at the reflux temperature of the organic solvent employed.

5. A process according to claim 1, wherein the inorganic persulfate is employed in catalytic amounts or in a molar ratio to the olefin within the range from 0.2:1 to 1:1.

6. A process according to claim 1, wherein the molar ratio of hypophosphorous acid to the olefin employed is within the range of 1:1 to 10:1, preferably within the range from 3:1 to 5:1.

7. A process according to claim 3, wherein an organic base selected from triethylamine, tri-n-butylamine and N-methylmorpholine is employed for maintenance of pH from 4.5 to 7.0.

8. A process according to claim 1, wherein the olefin is

9. A process according to claim 1, wherein the inorganic persulfate is employed in catalytic amounts or in a molar ratio to the olefin within the range from 0.2:1 to 0.5:1.

* * * * *